United States Patent [19]
Baird

[11] Patent Number: 5,294,236
[45] Date of Patent: Mar. 15, 1994

[54] EFFLUENT METERING SYSTEM
[75] Inventor: Thomas E. Baird, Springfield, Ill.
[73] Assignee: Baird Meter Inc., Springfield, Ill.
[21] Appl. No.: 32,828
[22] Filed: Mar. 10, 1993
[51] Int. Cl.⁵ .............................................. B01D 35/02
[52] U.S. Cl. ...................................... 55/270; 55/274; 55/374; 55/378; 55/484; 55/505
[58] Field of Search ................ 55/270, 274, 374, 378, 55/505, 484

[56] References Cited
U.S. PATENT DOCUMENTS

| | | | |
|---|---|---|---|
| 2,316,353 | 4/1943 | Moorhead | 55/378 X |
| 3,015,228 | 1/1962 | Shuttleworth et al. | 55/374 X |
| 3,597,903 | 8/1971 | Schaaf | 55/374 X |
| 3,877,900 | 4/1975 | Mitchell | 55/374 X |
| 4,157,252 | 6/1979 | Baird | 55/374 |
| 5,067,253 | 11/1991 | Hauch et al. | 55/274 X |

Primary Examiner—Charles Hart
Attorney, Agent, or Firm—Wood, Phillips, VanSanten, Hoffman & Ertel

[57] ABSTRACT

An effluent metering system includes an adapter connectable between the air outlet port on a vacuum cleaning appliance and a supplemental effluent metering device. The adapter preferably has a tubular shell which defines an inlet for receiving a flow of air discharged from the air outlet port. The adapter also has a pair of outlets. A first fluid passage in the shell connects the inlet with a first one of the outlets for exhausting air into a filter. A second fluid passage in the shell connects the inlet with a second one of the outlets for exhausting air into the supplemental metering device.

20 Claims, 3 Drawing Sheets

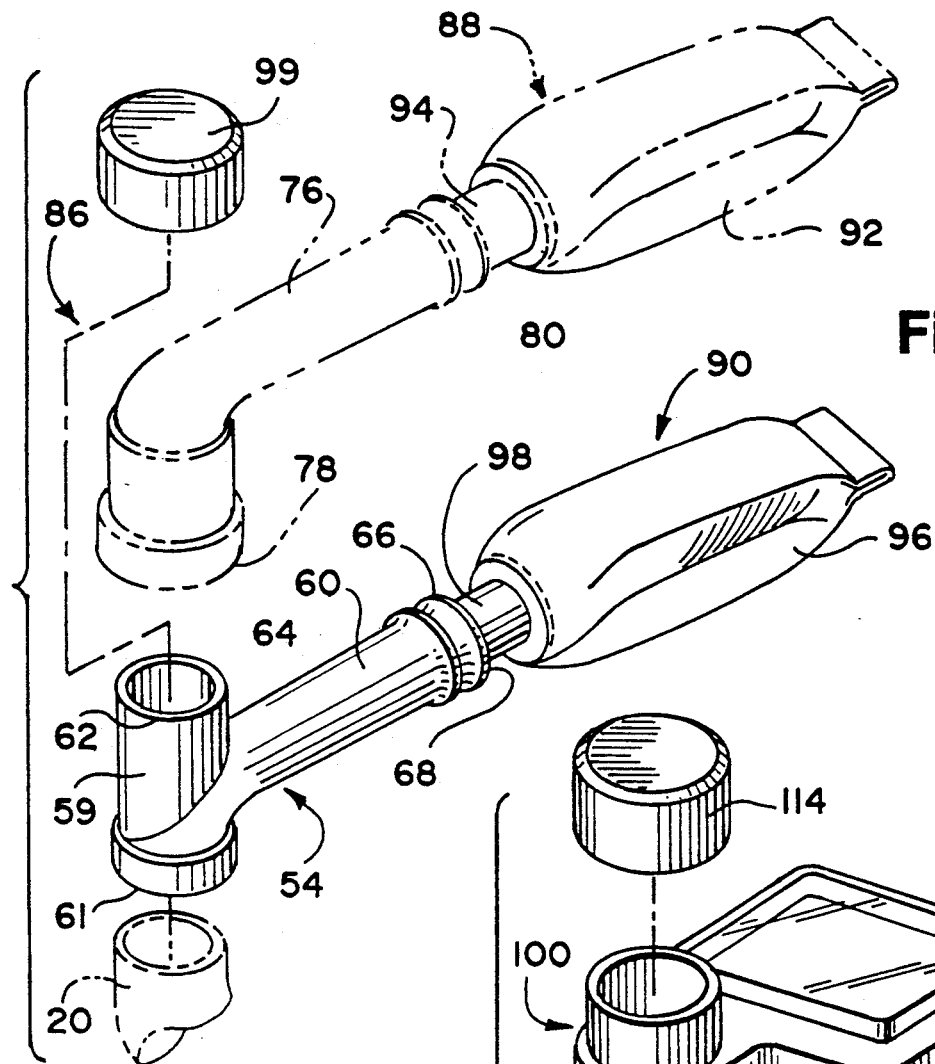
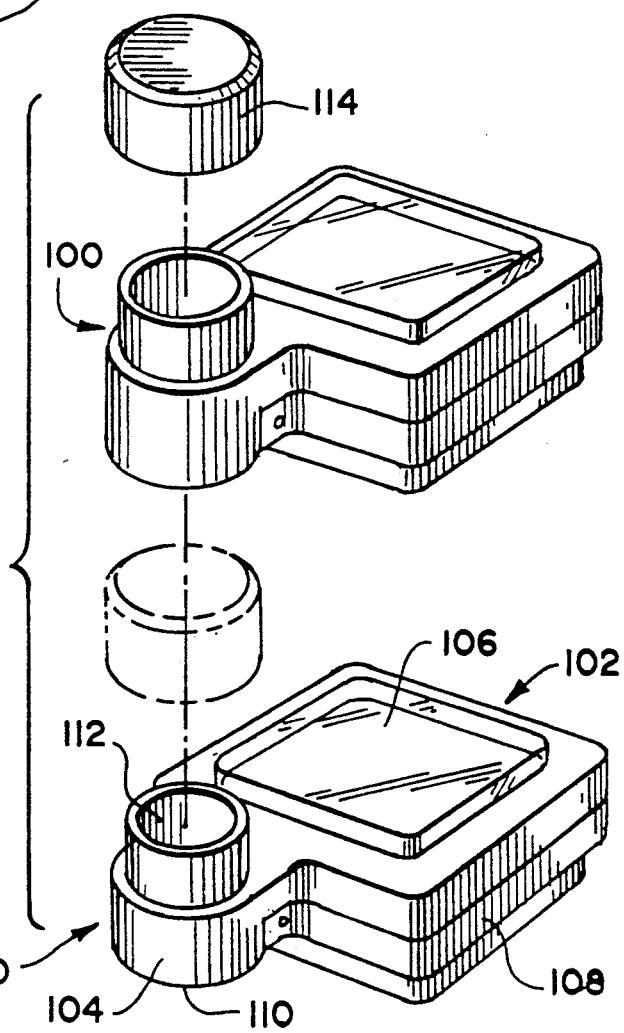

EFFLUENT METERING SYSTEM

FIELD OF THE INVENTION

This invention generally relates to the art of vacuum cleaners, and particularly, to an apparatus for demonstrating the effectiveness of a vacuum cleaner.

BACKGROUND OF THE INVENTION

Vacuum cleaning appliances (vacuum cleaners) are used to remove small particles of matter from the environment. Vacuum cleaners typically have an electrically powered fan unit designed to create a high velocity air stream through an inlet nozzle which causes a partial vacuum. The vacuum draws air, dust and other particulate material through the inlet nozzle. The air stream passes through some form of a filter, such as an air permeable bag, whereby material carried by the air stream is trapped on the filter.

As is generally known with regard to many types of appliances, the sale of vacuum cleaners is facilitated by demonstrating their effectiveness. For instance, a salesperson may perform a demonstration wherein a substance, such as sand, is intentionally deposited on a test area to be cleaned (for example, on a potential purchaser's carpet). The vacuum cleaner then is used to remove the substance and provide the potential purchaser with an example of the cleaner's capability. Effectiveness of a vacuum cleaner is demonstrated to a potential customer by 1) permitting the customer to examine the ultimate cleanliness of the test area, and 2) providing the customer with an indication of the amount of material trapped in the filter.

One technique for achieving the latter objective is to disconnect a vacuum bag from an air outlet port on a vacuum cleaner and to install an effluent metering device to the air outlet port. The vacuum then is operated and material drawn into the vacuum nozzle from a test area is discharged into the metering device. Visual inspection of effluent material in the metering device provides a potential purchaser with an indication of the effectiveness of the vacuum cleaner.

One known effluent metering device has an elongated tube which is connectable with the air outlet port on a vacuum cleaner fan unit. A clean test cloth is attached to an open end of the tube to form a bag which encloses the tube end. Such an apparatus for forming a bag with a test cloth is disclosed in Applicant's prior U.S. Pat. No. 4,157,252, issued Jun. 5, 1979. Air discharged by the fan unit passes through the test cloth while effluent material carried in the air stream is trapped on the test cloth. The test cloth is removed from the tube after the fan is deactivated, and a potential purchaser is allowed to inspect the test cloth.

Alternative effluent metering devices also have been proposed. For instance, rather than forming a bag with a test cloth, it is known to attach a preformed mini-bag directly to the end of bag forming tube. Further, enclosed housings having a disposable filter element, such as filter paper, have been used to demonstrate effluent retention in an effluent metering device.

Effluent metering devices of the type discussed above operate effectively only until the buildup of effluent material on the filter element (i.e., a test cloth, a mini-bag, or a filter paper) inhibits the flow of air through the element. Once the filter is clogged and air is prevented from flowing through the element, the metering device is rendered incapable of measuring additional effluent material. Moreover, reduced air flow through an effluent metering device not only limits the amount of material trapped by a filter element (and thus degrades the impact of the filter inspection part of a demonstration), but reduced air flow also decreases the suction power of the fan unit and thereby degrades the capability of a vacuum cleaner to remove a substance from a test area.

Prior effluent metering devices become blocked in an unacceptably short length of time. A need exists for an effluent metering device which provides increased capacity and useful operating life in order to enhance the impact of a vacuum cleaner demonstration.

SUMMARY OF THE INVENTION

It is an object of the present invention, therefore, to provide an improved effluent metering system for demonstrating the effectiveness of a vacuum cleaning appliance.

In the exemplary embodiment of the invention, an effluent metering system includes has an adapter connectable between the air outlet port on a vacuum cleaning appliance and a supplemental effluent metering device. The adapter preferably has a tubular shell which defines an inlet for receiving a flow of air discharged from the air outlet port. The adapter also has a pair of outlets. A first fluid passage in the shell connects the inlet with a first one of the outlets for exhausting air into a filter. A second fluid passage in the shell connects the inlet with a second one of the outlets for exhausting air into the supplemental metering device.

The invention contemplates that the adapter has a pair of integral tubes with each tube defining a separate fluid passage in the shell. In the exemplary form of the invention the adapter is made of plastic. A removable cap is provided for selectively closing the second outlet when a supplemental effluent metering device is not used.

The adapter has a friction fit with the air outlet port on a vacuum appliance and with the inlet of one or more effluent metering devices. In a modified form, the adapter has a bayonet-type connection wherein the adapter has slots for receiving pins on the air outlet port of a vacuum appliance.

The adapter can be used with different types of effluent metering devices. For instance, in one form of the invention the first outlet on the adapter is connected to an air permeable bag. In another form, an air permeable cloth is positioned to enclose the first outlet on the adapter and thereby trap effluent material carried in an outflow of air through the first outlet. In still another form, a housing having an inlet opening and an outlet opening is integral with the adapter. A paper filter in the housing traps effluent material carried in an airflow through the housing. The housing preferably has a window to facilitate observation of effluent trapped in the housing.

The invention further contemplates an effluent metering system having a plurality of adapters each for connecting an effluent metering device in parallel with an air outlet port on a vacuum cleaning appliance.

Other objects, features and advantages of the invention will be apparent from the following detailed description taken in connection with the accompanying drawings.

BRIEF DESCRIPTION OF THE DRAWINGS

The features of this invention which are believed to be novel are set forth with particularity in the appended claims. The invention, together with its objects and advantages, may be understood from the following description taken in conjunction with the accompanying drawings, in which like reference numerals identify like elements in the figures and in which:

FIG. 5 is an exploded perspective view showing the adapter in the effluent metering apparatus; and FIG. 6 is an exploded perspective view showing an alternative embodiment of the adapter.

DESCRIPTION OF THE PREFERRED EMBODIMENT

Figure 1:
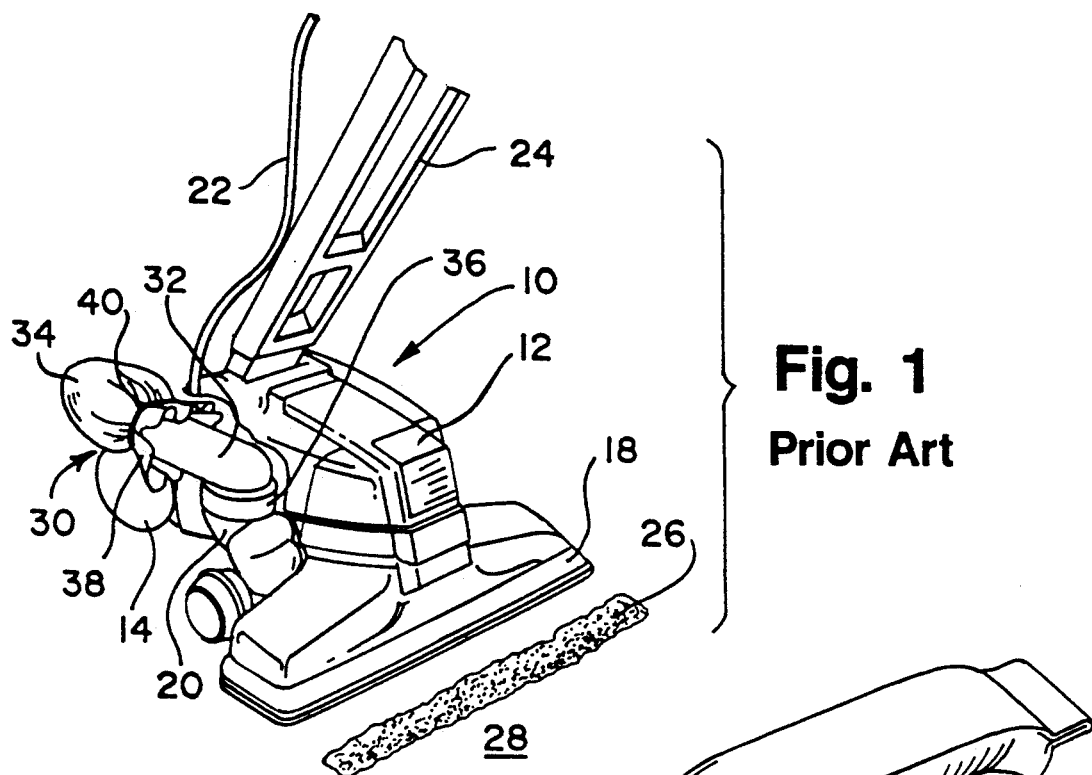
FIGS. 1-3 are diagrammatic illustrations of alternative prior art effluent metering devices.

A conventional vacuum cleaning appliance (or vacuum cleaner) is generally designated 10 in FIG. 1 and has an electrically powered fan unit 12 mounted on a pair of spaced-apart wheels 14 (one wheel shown in FIG. 1). Fan unit 12 has an inlet nozzle 18 through which matter is drawn into the fan unit and an air outlet port 20 through which a stream of air carrying effluent material exits the fan unit in a generally known manner. That is to say, fan unit 12 has a rotary fan which when activated by means of an electrical power cord 22 creates negative pressure or suction in nozzle 18 and creates positive pressure in air outlet port 20. A handle 24 extends upwardly from fan unit 12 and permits an individual to maneuver the fan unit while standing substantially upright.

Vacuum cleaner 10 in FIG. 1 is configured for demonstrating the effectiveness with which the vacuum cleaner can remove a quantity of dirt, such as sand 26, from a test area 28. In normal operation of the vacuum cleaner 10, an upright bag (not shown) would be connected to air outlet port 20 for trapping effluent material discharged by fan unit 12. Such a bag typically is mounted on handle 24 and is sufficiently large to permit the vacuum cleaner to be used repeatedly without requiring the bag to be emptied after each use. When the effectiveness of the vacuum cleaner is to be demonstrated, such as in the case of door-to-door sales, the relatively large upright bag is omitted and an effluent metering device, generally designated 30 in FIG. 1, is connected to air outlet port 20.

Effluent metering device 30 has an elongated tube 32 and an air permeable filter test cloth 34. An inlet end 36 of tube 32 is connected to air outlet port 20 by means of a friction fit therewith, or by a bayonet connection as described hereinafter. Filter test cloth 34 is positioned over a distal end 38 of tube 32 so as to form a bag for trapping solid material discharged from the tube. An elastic or coil spring band 40 secures filter cloth 34 to tube 32. Such a metering device is shown in U.S. Pat. No. 4,157,252, described above.

Figure 2:
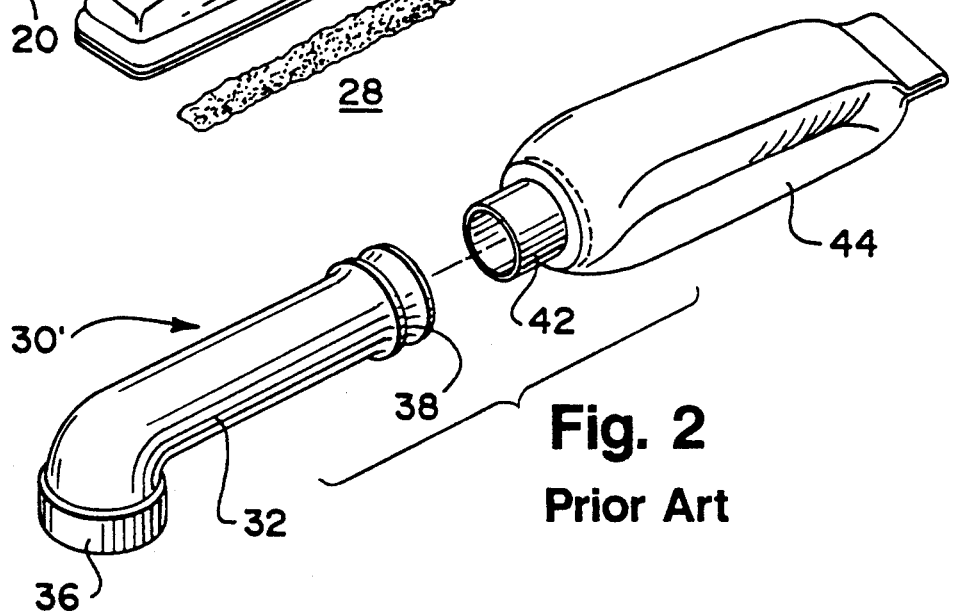
Figure 3:
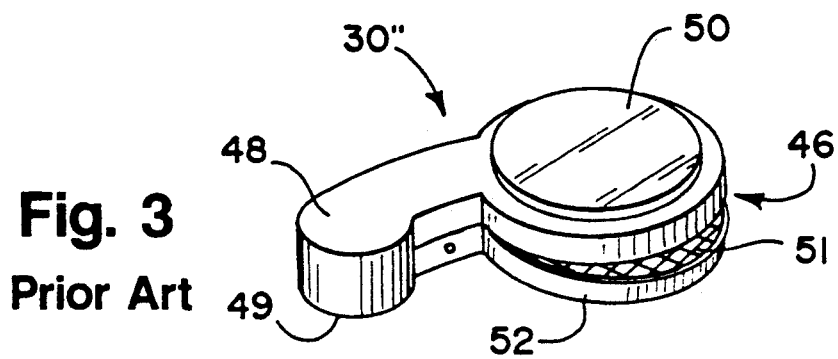

Alternative prior art effluent metering devices are illustrated in FIGS. 2 and 3.

Metering device 30' in FIG. 2 generally is similar to effluent metering device 30 and has an elongated tube 32 with an end 36 connectable with air outlet port 20. A cylindrical nipple 42 on a preformed mini-bag 44 is received in a distal end 38 of the tube.

Metering device 30'' in FIG. 3 has a filter assembly 46 integral with a tube 48. An inlet 49 on tube 48 is engageable with air outlet port 20 on fan unit 12. Filter assembly 46 has a window 50 for observing the contents of the assembly and a hinged tray 52 for receiving a disposable filter element, such as paper, between the tray and the window. Air discharged from fan unit 12 passes through tube 48 and exits filter assembly 46 through a screen 51 on tray 52 which supports a filter element. Effluent material carried by discharged air is trapped on the filter element.

Operation of the prior art metering devices shown in FIGS. 1-3 for performing a demonstration is summarized as follows. The inlet of a respective one of the metering devices 30, 30' or 30'' first is connected to air outlet port 20 on fan unit 12. Depending on the type of metering device utilized, a test cloth 34 (device 30), a mini-bag 44 (device 30') or a filter element (device 30''), the metering device is installed and a quantity of dirt 26 is deposited on test area 28. Fan unit 12 then is activated and vacuum cleaner 10 repeatedly is passed over the test area until as much of the dirt is removed therefrom as the particular metering device can handle. An observer of the demonstration then is permitted to examine test area 28 as well as the contents of the selected metering device 30, 30' or 30''.

the disclosed prior art effluent metering devices operate effectively only until the buildup of effluent material on the associated filter element blocks air flow through the device. Once the filter element is clogged and air is prevented from flowing freely through the metering device, the metering device is rendered incapable or at least ineffective of measuring additional effluent material. Moreover, reduced air flow through the effluent metering device not only limits the amount of material trapped by the filter element, but reduced air flow also decreases the suction power of the fan unit and thereby degrades the capability of the vacuum cleaner 10 to remove a substance, such as dirt 26, from test area 28. In other words, all of the demonstrative metering devices 30, 30' and 30'' of the prior art are considerably smaller than the normal vacuum cleaner collection bag. The metering devices fill-up more rapidly and give the impression that the vacuum cleaner has lost considerable power.

Figure 4:
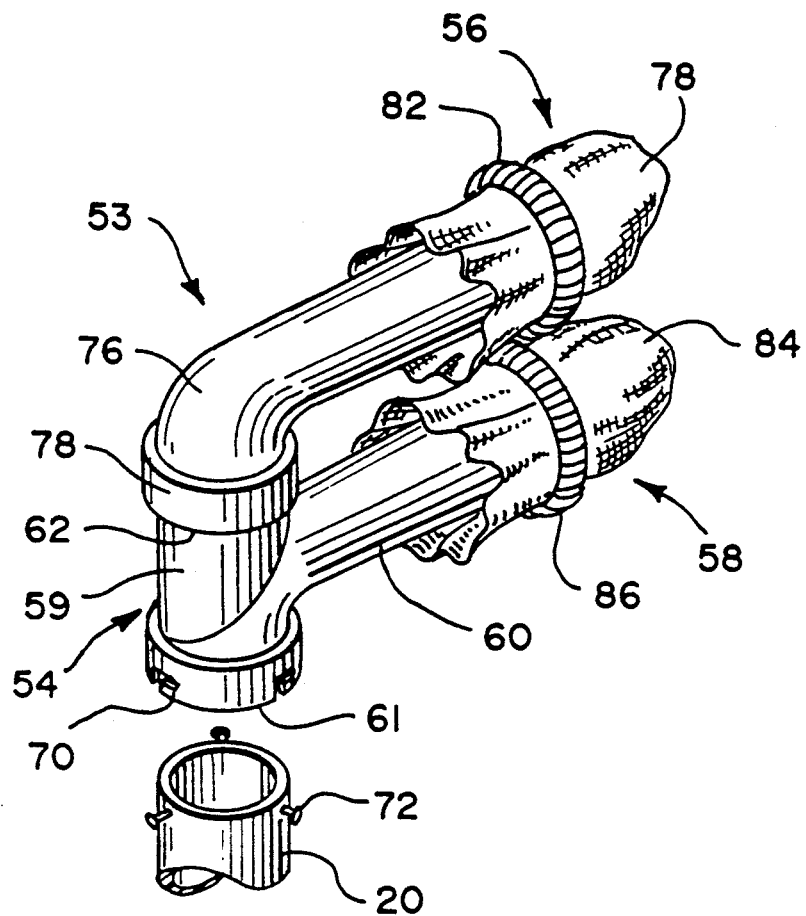
FIG. 4 is a perspective view of an effluent metering apparatus according to the present invention.

An effluent metering apparatus or system according to the present invention, generally designated 53 in FIG. 4, has an adapter 54 (also see FIG. 5) for interconnecting air outlet port 20 with a first effluent metering device 56 and a second effluent metering device 58.

Particularly, adapter 54 consists of a molded plastic shell having a pair of integral tubes 59 and 60. Tube 59 defines an inlet 61 on the shell for receiving air discharged from outlet port 20 as described hereafter. Tube 59 also has an outlet 62 and an internal fluid passage 64 connecting inlet 61 with outlet 62. Tube 60 has an outlet 66 and defines a fluid passage 68 connecting outlet 66 with passage 64 in tube 59.

Inlet 61 preferably is connected to air outlet port 20 by a bayonet connection, wherein tube 59 has a plurality of bayonet type grooves 70 and air outlet port 20 has a plurality of radial pins 72 each for engaging a corresponding one of the bayonet grooves to secure inlet 62 to air outlet port 20. Alternatively, and as shown in FIG. 5, inlet 61 and air outlet port 20 are connected by a friction fit therebetween. That is, the size of inlet 61 is selected such that an inner end surface of tube 59 frictionally engages an exterior surface on air outlet port 20.

First effluent metering device 56 has an elongated tube 76 attachable to outlet 62 on adapter 54. An inlet 78 on tube 76 preferably is connected to outlet 62 by a friction fit therebetween. The invention additionally contemplates other suitable means for connecting tube 76 with adapter 54, including the bayonet connection discussed above. An air permeable filter cloth 78 is positioned over an outlet end 80 of tube 76 to form a bag for trapping effluent material carried in a stream of air through the tube. An elastic band 82 secures filter cloth 78 to tube 76.

Second effluent metering device 58 has an air permeable filter cloth 84 positioned over outlet 66 on tube 60 to form a bag for trapping effluent material carried in a stream of air through the tube. An elastic band 86 secures filter cloth 84 to tube 60.

In one alternative embodiment, a mini-bag can be substituted for either or both of test cloths 78 and 84 (FIG. 4). More particularly, and as shown in FIG. 5, an alternative effluent metering system 86 has an adapter 54 for interconnecting air outlet port 20 with a first effluent metering device 88 and a second effluent metering device 90. Effluent metering device 88 includes a mini-bag 92 with an elongated nipple 94 inserted in outlet end 80 of tube 76. Effluent metering device 90 includes a second mini-bag 96 with an elongated nipple 98 inserted in outlet 66 on tube 60.

The adapter 54 thus provides a versatile construction wherein any combination of test cloths and mini-bags can be used to measure the amount of effluent material carried in an air stream discharged by a single vacuum cleaner. Further, multiple adapters 54 can be connected in series to interconnect more than two effluent metering devices. When it is desired to remove the tube 76 from an effluent metering system during the demonstration of a vacuum cleaner (such as to temporarily emphasize the amount of effluent material which is trapped solely by a metering device connected to adapter 54), a cap 99 is secured to adapter 54 and closes outlet 62 on tube 59.

The foregoing construction of adapter 54 advantageously provides the capability of selectively expanding the capacity of an effluent metering apparatus. For example, effluent metering apparatus 53 has twice the capacity of a prior art device having a single filter cloth. Consequently, a demonstration can be conducted for twice the length of time without clogging the filter cloth. In addition, each filter cloth 78 and 84 traps effluent material at the same rate since the devices 56 and 58 are connected in parallel. Thus, foreign matter discharged from air outlet port 20 distributes evenly between metering devices 56 and 58 and thereby maximizes the amount of time during which dual operation can be achieved. Similarly, effluent metering apparatus 86 has twice the capacity of a prior art device having a single mini-bag whereby a demonstration can be conducted for twice the length of time without clogging the mini-bags. Since the devices 88 and 90 are connected in parallel each mini-bag 92 and 96 traps effluent material at the same rate.

In another alternative embodiment (FIG. 6), an effluent metering device 100 has a filter assembly 102 with an integral connector 104 connectable in series between a supplementary metering device, such as a second effluent metering device 100, and air outlet port 20. Filter assembly 102 generally is similar to filter assembly 46 discussed above relative to FIG. 3 and has a window 106 for observing contents of the assembly and a hinged tray 108 for receiving a disposable filter element, such as paper, between the tray and the window. Integral connector 104 has an inlet 110 engageable with air outlet port 20 and an outlet 112 engageable with the inlet of the second metering device. A detachable cap 114 closes the outlet 112 of the upper metering device 100.

More than two metering devices 100 can be connected in series when additional demonstrative capability is required. For instance, cap 114 is removed from the upper metering device 100 and one or more additional metering devices are joined together in an upright stick. Cap 114 then is replaced on the outlet 112 of the uppermost metering device 100.

In addition to connecting two or more effluent metering devices 100 in series, the invention also contemplates the use of an effluent metering device 100 in combination with a metering device which has a filter test cloth, as shown in FIG. 4, or with a metering device which has a mini-bag, as shown in FIG. 5.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein.

I claim:

1. In a vacuum cleaning appliance having a housing with an opening through which matter is a drawn by a vacuum and an outlet port through which matter drawn into the housing is discharged outwardly thereof into a collection receptacle, the improvement comprising an adapter interchangeable with the collection receptacle for connecting an effluent metering device and a supplemental effluent metering device to said air outlet port, said adapter comprising:

a tubular shell defining an inlet for receiving effluent carrying air discharged from the outlet port of said vacuum cleaning appliance, a first outlet for exhausting air into said effluent metering device, and a second outlet for exhausting air into said supplemental effluent metering device; and means for connecting said first outlet to said effluent metering device and said second outlet to said supplemental effluent metering device externally of said housing to facilitate observation of effluent received in said effluent metering device and said supplemental effluent metering device.

2. The adapter of claim 1 in which the shell comprises a first tube having a first fluid passage connecting said inlet and said second outlet and a second tube having a second fluid passage connecting said first fluid passage and said first outlet.

3. The adapter of claim 2 in which the first tube is integral with the second tube.

4. The adapter of claim 1 in which the adapter is made of plastic.

5. The adapter of claim 1 in combination with a removable cap for selectively closing the second outlet when a supplemental effluent metering device is not connected thereto.

6. The adapter of claim 1 in which said means for interconnecting said shell comprises a surface on said shell having a shape adapted for frictional engagement with a surface on at least one of a vacuum cleaning appliance or an effluent metering device or a supplemental effluent metering device.

7. The adapter of claim 1 in which said means for interconnecting said shell comprises a plurality of pins on one of a) said shell or b) at least one of a vacuum cleaning appliance or an effluent metering device or a supplemental effluent metering device, and a plurality of locking grooves on the other of a) said shell or b) at least one of a vacuum cleaning appliance or an effluent metering device or a supplemental effluent metering device for receiving said pins.

8. An effluent metering device for demonstrating the amount of effluent material discharged through an outlet port on a vacuum cleaning appliance when matter drawn internally of said appliance is exhausted outwardly in a flow of air through said outlet port, said effluent metering device comprising:

an adapter having an inlet engageable with an air outlet port on a vacuum cleaning appliance and a first outlet engageable with a supplemental effluent metering device, said adapter defining a passageway through which air exhausted from said outlet port flows between said inlet and said first outlet, said adapter having a second outlet in fluid communication with said passageway; and filter means operatively associated with said adapter for removing effluent material from air flowing through said second outlet and located externally of the vacuum cleaning appliance to facilitate observation of effluent material removed by the filter means.

9. The effluent metering device of claim 8 in which the filter means is an air permeable bag with an opening therein connected to said second outlet for trapping effluent material carried in an outflow of air through said second outlet.

10. The effluent metering device of claim 8 in which the filter means is a sheet of air permeable cloth positioned to enclose the second outlet and thereby trap effluent material carried in an outflow of air through said second outlet.

11. The effluent metering device of claim 8 in which the filter means is a housing having an inlet opening connected to said second outlet and an outlet opening, said filter means having a filter element in the housing between said inlet opening and said opening for trapping effluent material carried in an outflow of air through said second outlet.

12. The effluent metering device of claim 11 in which said housing is integral with the adapter.

13. The effluent metering device of claim 11 in which the housing has window means for providing a visible indication of the amount of effluent material trapped by said filter element.

14. The effluent metering device of claim 11 in which the filter element is paper.

15. An effluent metering system for providing an indication of the amount of effluent material removed by a vacuum cleaning appliance, said effluent metering system comprising:

a first effluent metering device having a first inlet engageable with an air outlet port on a vacuum cleaning appliance and a first outlet, said first device having a passageway through which air flows between said first inlet and said first outlet, said first device having a second outlet in fluid communication with said passageway, and first filter means for removing effluent material carried in a flow of air through said first outlet; and a second effluent metering device having a second inlet engageable with the second outlet on said first effluent metering device, said second device having a third outlet and a passageway through which air flows between said second inlet and said third outlet, and second filter means for removing effluent material from a flow of air through said third outlet, at least one of said first and said second filter means including means for visibly demonstrating the amount of effluent material removed thereby while the vacuum cleaning appliance operates.

16. The effluent metering system of claim 15 in which at least one of said first filter means and said second filter means is an air permeable bag with an opening therein engageable with one of said first outlet on said first effluent metering device and said third outlet on said second effluent metering device.

17. The effluent metering system of claim 15 in which at least one of said first filter means and said second filter means is a sheet of air permeable cloth positioned to trap effluent material carried in an outflow of air through one of said first outlet on said first effluent metering device and said third outlet on said second effluent metering device.

18. The effluent metering system of claim 15 in which at least one of said first filter means and said second filter means is a housing having an inlet opening connected to one of said first outlet on said first effluent metering device and said third outlet on said second effluent metering device and an outlet opening, said one filter means having a filter element in the housing between said inlet opening and said outlet opening for trapping effluent material carried in a flow of air through said housing.

19. The effluent metering system of claim 15 in which said second effluent metering device has a fourth outlet for connection with a third effluent metering device.

20. The effluent metering system of claim 15 in which one of said first filter means and said second filter means is a sheet of air permeable cloth positioned to trap effluent material carried in an outflow of air through one of said first outlet on said first effluent metering device and said third outlet on said second effluent metering device, and in which the other of said first filter means and said second filter means is a housing having an inlet opening connected to the other of said first outlet on said first effluent metering device and said third outlet on said second effluent metering device and an outlet opening, said other filter means having a filter element in the housing between said inlet opening and said outlet opening for trapping effluent material carried in a flow of air through said housing and window means for demonstrating the amount of effluent material trapped by said filter element.

* * * * *